United States Patent [19]

Raddatz et al.

[11] Patent Number: 4,812,555

[45] Date of Patent: Mar. 14, 1989

[54] PEPTIDES POSSESSING RENIN INHIBITORY ACTIVITY

[75] Inventors: Peter Raddatz, Darmstadt; Günter Hölzemann, Seeheim; Alfred Jonczyk, Darmstadt; Claus J. Schmitges, Groß-Umstadt; Klaus O. Minck, Ober-Ramstadt, all of Fed. Rep. of Germany

[73] Assignee: Merck Patent Gesellschaft mit Beschrankter Haftung, Darmstadt, Fed. Rep. of Germany

[21] Appl. No.: 171,973

[22] Filed: Mar. 22, 1988

Related U.S. Application Data

[63] Continuation of Ser. No. 925,596, Oct. 31, 1986, abandoned.

[30] Foreign Application Priority Data

Oct. 31, 1985 [DE] Fed. Rep. of Germany ....... 3538749

[51] Int. Cl.$^4$ .............................................. A61K 37/02
[52] U.S. Cl. .................... 530/323; 530/330; 530/331; 530/332

[58] Field of Search ............... 530/323, 330, 331, 332; 514/17, 18

[56] References Cited

U.S. PATENT DOCUMENTS 4,636,491 1/1987 Bock et al. ........................ 514/16

FOREIGN PATENT DOCUMENTS 077028 4/1983 European Pat. Off. .
0155809 9/1985 European Pat. Off. .
WO/03004 8/1984 World Int. Prop. O. .

*Primary Examiner*—John Kight
*Assistant Examiner*—Nathan M. Nutter
*Attorney, Agent, or Firm*—Millen & White

[57] ABSTRACT

New peptides of the formula I

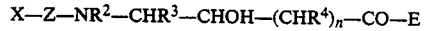

$$X-Z-NR^2-CHR^3-CHOH-(CHR^4)_n-CO-E$$

wherein X, Z, $R^2$, $R^3$, $R^4$, E and n are as defined herein and their salts inhibit the activity of human plasma renin.

24 Claims, No Drawings

PEPTIDES POSSESSING RENIN INHIBITORY ACTIVITY

This application is a continuation of parent application Ser. No. 925,596 filed Oct. 31, 1986, now abandoned.

BACKGROUND OF THE INVENTION

The invention relates to new peptides. Similar compounds are known from European Pat. No. A-77,028.

SUMMARY OF THE INVENTION

It is an object of this invention to provide new compounds with useful properties, in particular to those which can be used for the preparation of medicaments.

Upon further study of the specification and appended claims, further objects and advantages of this invention will become apparent to those skilled in the art.

These objects have been achieved by providing new peptides of the formula I

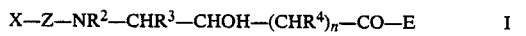

$$X-Z-NR^2-CHR^3-CHOH-(CHR^4)_n-CO-E \quad I$$

wherein

X is H, $R^1-O-C_mH_{2m}-CO-$, $R^1-C_mH_{2m}-O-CO-$, $R^1-C_mH_{2m}-CO-$, $R^1-SO_2-$, $(R^1-C_mH_{2m})-L(R^1-C_pH_{2p})-C_rH_{2r}-CO-$, $H-(NHCH_2CH_2)_m-NH-CH_2CO-$ or 9-fluorenyl-$C_mH_{2m}-O-CO-$, Z is 1 to 4 amino acid radicals which are bonded to one another in peptide form and chosen independently from Abu, Ada, Ala, Arg, Asn, Bia, Cal, Dab, Gln, Gly, His, N(im)-alkyl-His, Ile, Leu, tert.-Leu, Lys, Met, αNal, βNal, Nbg, Nle, Orn, Phe, Pro, Ser, Thr, Tic, Trp, Tyr or Val, E is OH, OA, $NH_2$, NHA or $NA_2$, $R^1$ is H, A, Ar, Ar-alkyl, cycloalkyl which has 3 to 7 C atoms and is unsubstituted or mono- or polysubstituted by alkyl, alkoxy and/or Hal, cycloalkyl-alkyl with 4–11 C atoms, bicycloalkyl or tricycloalkyl with in each case 7–14 C atoms or bicycloalkylalkyl or tricycloalkylalkyl with in each case 8–18 C atoms, wherein the group $(R^1-C_mH_{2m})-L(R^1-C_pH_{2p})$ also can be pyrrolidino, piperidino, morpholino or thiomorpholino, $R^2$ and $R^4$ are each independently H or A, $R^3$ is cycloalkylalkyl, bicycloalkylalkyl or tricycloalkylalkyl with in each case up to 18 C atoms, L is CH or N, M, p and r are each independently 0, 1, 2, 3, 4 or 5, n is 1 or 2, Ar is phenyl which is unsubstituted or mono- or polysubstituted by A, AO, Hal, $CF_3$, OH and/or $NH_2$, or unsubstituted naphthyl, Hal is F, Cl, Br or I and A is alkyl with 1–8 C atoms, and wherein, furthermore, one or more —NH—CO— groups can also be replaced by one or more —N(alkyl)—CO— groups, and the A and Hal groups can be the same or different, and salts thereof.

DETAILED DISCUSSION

It has been found that the compounds of the formula I and their salts have very useful properties. In particular, they inhibit the activity of human plasma renin. This action can be demonstrated, for example, by the method of F. Fyhrquist et al., Clin. Chem. 22, 250–256 (1976). It is remarkable that these compounds are very specific inhibitors of renin; as a rule substantially higher concentrations of these compounds are necessary for inhibition of other aspartyl proteinases (for example pepsin and cathepsin D), concentrations about 100 to 10,000 times as high.

The compounds can be used as medicament active compounds in human and veterinary medicine, in particular for the prophylaxis and for the treatment of cardiac, circulatory and vascular diseases, above all hypertension, cardiac insufficiency and hyperaldosteronism. The compounds can also be used for diagnostic purposes in order to determine the possible contribution of the renin activity towards maintaining the pathological state in patients with hypertension or hyperaldosteronism. Such diagnostic tests can be performed in the manner disclosed in EP-A-77,028.

The amino acid radical abbreviations given above and below represent the radicals —NH—CHR—CO— (wherein R has the specific meaning known for each amino acid) of the following amino acids:

Abu 2-aminobutyric acid
Ada adamantylalanine
Ala alanine
Arg arginine
Asn asparagine
Bia benzimidazolylalanine
Cal cyclohexylalanine
Dab 2,4-diaminobutyric acid
Gln glutamine
Gly glycine
His histidine
N(im)-alkyl-His histidine substituted by A in the 1- or 3-position of the imidazole ring
Ile isoleucine
Leu leucine
tert.-Leu tert.-leucine
Lys lysine
Met methionine
αNal α-naphthylalanine
βNal β-naphthylalanine
Nbg (2-norbornyl)-glycine
Nle norleucine
N-Me-His N-methyl-histidine
N-Me-Phe N-methyl-phenylalanine
Orn ornithine
Phe phenylalanine
Pro proline
Ser serine
Thr threonine
Tic tetrahydroisoquinoline-1-carboxylic acid
Trp tryptophan
Tyr tyrosine
Val valine.

Furthermore, the symbols below have the following meanings:

BOC tert.-butoxycarbonyl
imi-BOM benzyloxymethyl in the 1-position of the imidazole ring
CBZ benzyloxycarbonyl
DNP 2,4-dinitrophenyl
imi-DNP 2,4-dinitrophenyl in the 1-position of the imidazole ring
FMOC 9-fluorenylmethoxycarbonyl
OMe methyl ester
OEt ethyl ester
POA phenoxyacetyl
DCCI dicyclohexylcarbodiimide
HOBt 1-hydroxybenzotriazole.

Where the abovementioned amino acids can occur in several enantiomeric forms, all these forms and also their mixtures (for example the DL forms) are included above and below, for example as a constituent of the compounds of the formula I. The L forms are preferred. Where individual compounds are listed below, the abbreviations of these amino acids in each case relate to the L form, unless expressly indicated otherwise.

The radicals and parameters X, Z, E, $R^1$ to $R^4$, L, m, n, p, r, Ar, Hal, A, $G^1$, $G^2$, $Z^1$, $Z^2$ and W above and below have the meanings given in the case of the formulae I, II or III, unless expressly indicated otherwise.

In the above formulae, A has 1-8, preferably 1, 2, 3 or 4, C atoms. A is preferably methyl, or furthermore ethyl, propyl, isopropyl, butyl, isobutyl, sec.-butyl or tert.-butyl, or moreover also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl or 1,1,2- or 1,2,2-trimethylpropyl.

Cycloalkyl preferably is cyclopropyl, cyclobutyl, cyclopentyl, cyclohexyl or cycloheptyl, but also, for example, 1-, 2- or 3-methylcyclopentyl or 1-, 2-, 3- or 4-methylcyclohexyl.

Cycloalkyl-alkyl accordingly preferably is cyclopropylmethyl, 2-cyclopropylethyl, cyclobutylmethyl, 2-cyclobutylethyl, cyclopentylmethyl, 2-cyclopentylethyl, cyclohexylmethyl or 2-cyclohexylethyl, but also, for example, 1-, 2- or 3-methylcyclopentylmethyl or 1-, 2-, 3- or 4-methylcyclohexylmethyl.

Bicycloalkyl preferably is 1- or 2-decalyl, 2-bicyclo[2,2,1]heptyl or 6,6-dimethyl-2-bicyclo[3,1,1]heptyl.

Tricycloalkyl preferably is 2-adamantyl.

Ar preferably is phenyl, or furthermore, preferably, o-, m- or p-tolyl, o-, m- or p-ethylphenyl, o-, m- or p-methoxyphenyl, o-, m- or p-fluorophenyl, o-, m- or p-chlorophenyl, o-, m- or p-bromophenyl, o-, m- or p-iodophenyl, o-, m- or p-trifluoromethylphenyl, 2,3-, 2,4-, 2,5-, 2,6-, 3,4- or 3,5-dimethoxyphenyl, 3,4,5-trimethoxyphenyl, o-, m- or p-aminophenyl or 1- or 2-naphthyl.

$R^1$ preferably is A, in particular methyl, ethyl, propyl, isopropyl, butyl, isobutyl or tert.-butyl, or furthermore preferably cyclopropyl, cyclopentyl, cyclohexyl, phenyl or benzyl.

$R^2$ and $R^4$ preferably are H or methyl, or furthermore ethyl, propyl, isopropyl, butyl or isobutyl.

$R^3$ preferably is cyclohexylmethyl, or furthermore preferably 2-cyclohexylethyl, bicyclo[2,2,1]heptyl-2-methyl or 6,6-dimethylbicyclo[3,1,1]heptyl-2-methyl.

m, p and r are preferably 0, 1 or 2; n is preferably 1.

X preferably is H, POA, alkoxycarbonyl, such as BOC, CBZ, alkanoyl, such as acetyl, propionyl, butyryl or isobutyryl, cycloalkylcarbonyl, such as cyclopentylcarbonyl or cyclohexylcarbonyl, aroyl, such as benzoyl, arylalkanoyl, such as phenylacetyl, 2- or 3-phenylpropionyl, 4-phenylbutyryl, 2-benzyl-3-phenylpropionyl, 2-benzyl-4-phenylbutyryl, 2-(2-phenylethyl)-4-phenylbutyryl, 2-(2-naphthylmethyl)-4-phenylbutyryl, 2- or 3-o-, -m- or -p-fluorophenylpropionyl, 2- or 3-o-, -m- or -p-chlorophenylpropionyl, or cycloalkylalkanoyl, such as cyclohexylacetyl or 2- or 3-cyclohexylpropionyl. Particularly preferred radicals X are H and BOC, and furthermore POA, 4-phenylbutyryl, 2-benzyl-3-phenylpropionyl, 2-benzyl-4-phenylbutyryl, 2-(2-phenylethyl)-4-phenylbutyryl), 2-(2-naphthylmethyl)-4-phenylbutyryl and CBZ.

Z preferably is 2, but also 1, or furthermore 3 or 4 amino acid radicals which are bonded to one another in peptide form, in particular one of the groups His, Phe-His, Pro-Phe-His or His-Pro-Phe-His, or furthermore preferably the groups Abu, Ada, Asn, Bia, Cal, Gln, N-(im)-alkyl-His, Leu, αNal, βNal, Nle, Phe, Trp, Tyr, Abu-His, Ada-His, Ala-His, Ala-Phe, Arg-His, Asn-His, Bia-His, Cal-His, Dab-His, Gly-His, His-His, Ile-His, Leu-His, tert.-Leu-His, Lys-His, Met-His, αNal-His, βNal-His, Nbg-His, Nle-His, (N-Me-His)-His, (N-Me-Phe)-His, Orn-His, Phe-Abu, Phe-Ada, Phe-Ala, Phe-Arg, Phe-Asn, Phe-Bia, Phe-Cal, Phe-Dab, Phe-Gln, Phe-Gly, Phe-(N-im-alkyl-His), Phe-Ile, Phe-Leu, Phe-tert.-Leu, Phe-Lys, Phe-Met, Phe-α-Nal, Phe-βNal, Phe-Nbg, Phe-Nle, Phe-(N-Me-His), Phe-(N-Me-Phe), Phe-Orn, Phe-Phe, Phe-Pro, Phe-Ser, Phe-Thr, Phe-Tic, Phe-Trp, Phe-Tyr, Phe-Val, Pro-His, Ser-His, Thr-His, Tic-His, Trp-His, Tyr-His or Val-His, or furthermore Ada-Phe-His, Pro-Ala-His, Pro-Ala-Phe, Pro-Phe-Ala, Pro-Phe-Phe, His-Pro-Ala-His, His-Pro-Ala-Phe, His-Pro-Phe-Ala or His-Pro-Phe-Phe, or moreover Pro-Abu-His, Pro-Ada-His, Pro-Arg-His, Pro-Asn-His, Pro-Bia-His, Pro-Dab-His, Pro-Gly-His, Pro-His-His, Pro-Ile-His, Pro-Leu-His, Pro-tert.-Leu-His, Pro-Lys-His, Pro-Met-His, Pro-Nbg-His, Pro-Nle-His, Pro-(N-Me-His)-His, Pro-(N-Me-Phe)-His, Pro-Orn-His, Pro-Phe-Abu, Pro-Phe-Ada, Pro-Phe-Arg, Pro-Phe-Asn, Pro-Phe-Bia, Pro-Phe-Dab, Pro-Phe-Gln, Pro-Phe-Gly, Pro-Phe-(N-im-alkyl-His), Pro-Phe-Ile, Pro-Phe-Leu, Pro-Phe-tert.-Leu, Pro-Phe-Lys, Pro-Phe-Met, Pro-Phe-Nbg, Pro-Phe-Nle, Pro-Phe-(N-Me-His), Pro-Phe-(N-Me-Phe), Pro-Phe-Orn, Pro-Phe-Pro, Pro-Phe-Ser, Pro-Phe-Thr, Pro-Phe-Tic, Pro-Phe-Trp, Pro-Phe-Tyr, Pro-Phe-Val, Pro-Pro-His, Pro-Ser-His, Pro-Thr-His, Pro-Tic-His, Pro-Trp-His, Pro-Tyr-His, Pro-Val-His, His-Pro-Abu-His, His-Pro-Ada-His, His-Pro-Arg-His, His-Pro-Asn-His, His-Pro-Bia-His, His-Pro-Dab-His, His-Pro-Gly-His, His-Pro-His-His, His-Pro-Ile-His, His-Pro-Leu-His, His-Pro-tert.-Leu-His, His-Pro-Lys-His, His-Pro-Met-His, His-Pro-Nbg-His, His-Pro-Nle-His, His-Pro-(N-Me-His)-His, His-Pro-(N-Me-Phe)-His, His-Pro-Orn-His, His-Pro-Phe-Abu, His-Pro-Phe-Ada, His-Pro-Phe-Arg, His-Pro-Phe-Asn, His-Pro-Phe-Bia, His-Pro-Phe-Dab, His-Pro-Phe-Gln, His-Pro-Phe-Gly, His-Pro-Phe(N-im-alkyl-His), His-Pro-Phe-Ile, His-Pro-Phe-Leu, His-Pro-Phe-tert.-Leu, His-Pro-Phe-Lys, His-Pro-Phe-Met, His-Pro-Phe-Nbg, His-Pro-Phe-Nle, His-Pro-Phe-(N-Me-His), His-Pro-Phe-(N-Me-Phe), His-Pro-Phe-Orn, His-Pro-Phe-Pro, His-Pro-Phe-Ser, His-Pro-Phe-Thr, His-Pro-Phe-Tic, His-Pro-Phe-Trp, His-Pro-Phe-Tyr, His-Pro-Phe-Val, His-Pro-Pro-His, His-Pro-Ser-His, His-Pro-Thr-His, His-Pro-Tic-His, His-Pro-Trp-His, His-Pro-Tyr-His or His-Pro-Val-His.

E is preferably OH, $OCH_3$, $OC_2H_5$, $NH_2$, $NHCH_3$ or $N(CH_3)_2$.

The group W is preferably —NH—$CHR^3$—CHOH—$CH_2$—CO—, in particular —NH—CH(cyclohexylmethyl)—CHOH—$CH_2$—CO— ("AHCP", derived from 4-amino-3-hydroxy-5-cyclohexylpentanoic acid) or —NH—CH($CH_2CH_2$-cyclohexyl)—CHOH—$CH_2$—CO— ("AHCH"; derived from 4-amino-3-hydroxy-6-cyclohexylhexanoic acid).

The group W has at least two chiral centers. The compounds of the formula I can therefore occur in various—optically inactive or optically active—forms. Formula I includes all these forms. If W is —NH—CH$R^3$—CHOH—$CH_2$—CO—, the 3S-hydroxy-4S-amino enantiomers are preferred. Unless indicated otherwise in the designation of the individual substances, the abbreviations AHCP and AHCH always relate to these 3S,4S forms.

The preferred number of substituents in the substituted cycloalkyl and phenyl groups mentioned above is 1 to 3, more preferably 1 or 2.

The invention accordingly particularly relates to those compounds of the formula I in which at least one of the radicals mentioned has one of the abovementioned preferred meanings. Some preferred groups of compounds can be expressed by the following part formulae Ia to If, which correspond to the formula I but wherein in Ia X is H, POA, BOC, 4-phenylbutyryl, 2-benzyl-3-phenylpropionyl, 2-benzyl-4-phenylbutyryl, 2-(2-phenylethyl)-4-phenylbutyryl, 2-(2-naphthylmethyl)-4-phenylbutyryl or CBZ, Z is His, Ada-His, Cal-His, Nle-His, Phe-Abu, Phe-Dab, Phe-His, Phe-Lys, Phe-Met, Phe-(N-im-methyl)-His, Phe-Nle, Phe-Orn, Pro-Phe-His or His-Pro-Phe-His, $R^2$ and $R^4$ are each H, $R^3$ is cyclohexylmethyl or 2-cyclohexylethyl, E is OH, OMe, OEt, $NH_2$, $NH(CH_3)$ or $N(CH_3)_2$ and n is 1;

in Ib

X is H, BOC, 2-benzyl-3-phenylpropionyl, 2-benzyl-4-phenylbutyryl, 2-(2-phenylethyl)-4-phenylbutyryl or 2-(2-naphthylmethyl)-4-phenylbutyryl, Z is His, Ada-His, Cal-His, Nle-His, Phe-Abu, Phe-Dab, Phe-His, Phe-Lys, Phe-Met, Phe-(N-im-methyl)-His, Phe-Nle or Phe-Orn, $R^2$ and $R^4$ are each H, $R^3$ is cyclohexylmethyl, E is OH, OMe, OEt, $NH_2$, $NH(CH_3)$ or $N(CH_3)_2$ and n is 1;

in Ic

X is H, BOC or 2-benzyl-4-phenylbutyryl,

Z is His, Phe-Nle or Phe-His, $R^2$ and $R^4$ are each H, $R^3$ is cyclohexylmethyl, E is OH, OMe, OEt, $NH_2$, $NH(CH_3)$ or $N(CH_3)_2$ and n is 1;

in Id

X is BOC or 2-benzyl-4-phenylbutyryl,

Z is His, Phe-Nle or Phe-His, $R^2$ and $R^4$ are each H, $R^3$ is cyclohexylmethyl, E is OH, OMe, $NH_2$ or $N(CH_3)_2$ and n is 1;

in Ie

X is BOC,

Z is Phe-Nle or Phe-His, $R^2$ and $R^4$ are each H, $R^3$ is cyclohexylmethyl,

E is OH or OME and n is 1;

if If

X is pyrrolidinocarbonyl, piperidinocarbonyl, morpholinocarbonyl or thiomorpholinocarbonyl.

The invention furthermore relates to a process for the preparation of a peptide of the formula I and of its salts, characterized in that it is liberated from one of its functional derivatives by treatment with a solvolyzing or hydrogenolyzing agent, or in that a compound which corresponds to the formula I but contains one or more additional C—C and/or C—N and/or C—O bonds instead of H atoms is reduced, or in that a carboxylic acid of the formula II $$X—G^1—OH \qquad II$$

wherein $G^1$ is (a) $Z^1$ or (b) Z is reacted with an amino compound of the formula III $$H—G^2 \qquad III$$

wherein $G^2$ is (a) $Z^2$—W—E or (b) W—E,

W is —$NR^2$—$CHR^3$—CHOH—$(CHR^4)_n$—CO— and $Z^1+Z^2$ together are Z, and in that, if appropriate, in a compound of the formula I, a functionally modified amino and/or hydroxyl group is liberated by treatment with solvolysing or hydrogenolysing agents, and/or a radical E is converted into another radical E by treatment with esterifying, solvolysing or amidating agents, and/or a compound of the formula I is converted into one of its salts by treatment with an acid or base.

The compounds of the formula I and also the starting substances for their preparation are moreover prepared by methods which are known per se, such as are described in the literature (for example in the standard works, such as Houben-Weyl, Methoden der Organischen Chemie (Methods of Organic Chemistry), Georg-Thieme-Verlag, Stuttgart; and furthermore European Pat. No. A-45,665, European Pat. No. A-77,028, European Pat. No. A-77,029 and European Pat. No. A-81,783), and in particular under reaction conditions which are known and suitable for the reactions mentioned. Variants which are known per se and are not mentioned here in more detail can also thereby be used.

If desired, the starting substances can also be formed in situ, so that they are not isolated from the reaction mixture but are immediately reacted further to give the compounds of the formula I.

The compounds of the formula I are preferably obtained by being liberated from their functional derivatives by solvolysis, in particular hydrolysis, or by hydrogenolysis.

Preferred starting substances for the hydrolysis or hydrogenolysis are those which contain corresponding protected amino and/or hydroxyl groups instead of one or more free amino and/or hydroxyl groups, preferably those which carry an amino-protective group instead of an H atom bonded to an N atom, for example those which correspond to the formula I but contain an N(im-)—$R^5$—His group (wherein $R^5$ is an amino-protective group, for example BOM or DNP) instead of an His group.

Starting substances which contain a hydroxyl-protective group instead of the H atom of a hydroxyl group, for example those of the formula X—Z—$NR^2$—CHR$^3$—CHOR$^6$—$(CHR^4)_n$—CO—E, wherein $R^6$ is a hydroxyl-protective group, are furthermore preferred.

It is also possible for the molecule of the starting substance to contain several—identical or different—protected amino and/or hydroxyl groups. If the protective groups present differ from one another, they can in many cases be split off selectively.

The term "amino-protective group" is generally known and relates to groups which are suitable for protecting (for blocking) an amino group from chemical reactions but which can easily be removed when the desired chemical reaction has been carried out elsewhere in the molecule. Typical such groups are, in particular, unsubstituted or substituted acyl, aryl (for example 2,4-dinitrophenyl), aralkoxymethyl (for example benzyloxymethyl) or aralkyl groups (for example benzyl, 4-nitrobenzyl or triphenylmethyl). Since the amino-protective groups are removed after the desired reaction (or reaction sequence), their nature and size is otherwise not critical; those with 1-20, in particular 1-8, C atoms, however, are preferred. The term "acyl group" is to be interpreted in the broadest sense in connection with the present process. It includes acyl groups derived from aliphatic, araliphatic, aromatic or heterocyclic carboxylic acids or sulphonic acids, and, in particular, alkoxycarbonyl, aryloxycarbonyl and, above all, aralkoxycarbonyl groups. Examples of such acyl groups are alkanoyl, such as acetyl, propionyl or butyryl; aralkanoyl, such as phenylacetyl; aroyl, such as benzoyl or toluyl; aryloxyalkanoyl, such as phenoxyacetyl; alkoxycarbonyl, such as methoxycarbonyl, ethoxycarbonyl, 2,2,2-trichloroethoxycarbonyl, BOC, 2-iodoethoxycarbonyl; and aralkoxycarbonyl, such as CBZ ("carbobenzoxy"), 4-methoxybenzyloxycarbonyl or FMOC. Preferred amino-protective groups are DNP, BOM, CBZ, FMOC, benzyl and acetyl.

The term "hydroxyl-protective group" is likewise generally known and relates to groups which are suitable for protecting a hydroxyl group from chemical reactions but which can easily be removed when the desired chemical reaction has been carried out elsewhere in the molecule. Typical examples of such groups are the abovementioned unsubstituted or substituted aryl, aralkyl or acyl groups, and furthermore also alkyl groups. The nature and size of the hydroxyl-protective groups is not critical, since they are removed again after the desired chemical reaction or reaction sequence; groups with 1-20, in particular 1-10, C atoms are preferred. Examples of hydroxyl-protective groups are, inter alia, benzyl, p-nitrobenzoyl, p-toluenesulphonyl and acetyl, benzyl and acetyl being particularly preferred.

The hydroxyl group can also be part of a carboxyl group, so that a carboxyl-protective group is used as the hydroxyl-protective group. The carboxyl group can thus be bonded to a polymer, for example in ester form, in accordance with the "Merrifield" synthesis principle.

The functional derivatives of the compounds of the formula I to be used as starting substances can be prepared by customary methods of amino acid and peptide synthesis, such as are described, for example, in the standard works and patent applications mentioned.

The liberation of the compounds of the formula I from their functional derivatives is effected—depending on the protective group used—with, for example, strong acids, advantageously with trifluoroacetic acid or perchloric acid, but also with other strong inorganic acids, such as hydrochloric acid or sulphuric acid, strong organic carboxylic acids, such as trichloroacetic acid, or sulphonic acids, such as benzenesulphonic or p-toluenesulphonic acid. It is possible but not always necessary for an addition inert solvent to be present. Suitable inert solvents are, preferably, organic solvents, for example carboxylic acids, such as acetic acid, ethers, such as tetrahydrofuran or dioxane, amides, such as dimethylformamide (DMF), halogenated hydrocarbons, such as methylene chloride, and furthermore also alcohols, such as methanol, ethanol or isopropanol, and water. Mixtures of the above-mentioned solvents are also suitable. Trifluoroacetic acid is preferably used in excess without the addition of another solvent, and perchloric acid is prefereably used in the form of a mixture of acetic acid and 70% perchloric acid in a ratio of 9:1. The reaction temperatures for the splitting reaction are advantageously between about 0° and about 50°, and the reaction is preferably carried out between 15° and 30° (room temperature).

The BOC group, can preferably be split off, for example, with 40% trifluoroacetic acid in methylene chloride or with about 3 to 5N HCl in dioxane at 15°-30°, and the FMOC group can preferably be split off with an approximately 5 to 20% solution of dimethylamine, diethylamine or pyridine in DMF at 15°-30°. The DNP group is also split off, for example, with an approximately 3 to 10% solution of 2-mercaptoethanol in DMF/water at 15°-30°. In the "Merrifield" method, compounds of the formula I (E=OH) are advantageously split off from the polymeric carrier with trifluoroacetic acid.

Protective groups which can be removed hydrogenolytically (for example BOM, CBZ or benzyl) can be split off, for example, by treatment with hydrogen in the presence of a catalyst (for example a noble metal catalyst, such as palladium, advantageously on a support, such as charcoal). Suitable solvents for this reaction are those mentioned above, in particular, for example, alcohols, such as methanol or ethanol, or amides, such as DMF. The hydrogenolysis is as a rule carried out at temperatures between about 0° and 100° under pressures between about 1 and 200 bar, preferably at 20°-30° under 1-10 bar. Hydrogenolysis of the CBZ group is effected well, for example, over 5-10% Pd-C in methanol at 20°-30°.

The compounds of the formula I can also be obtained by reduction of corresponding compounds which contain one or more additional C—C and/or C—N and/or C—O bonds instead of H atoms.

Thus, for example, keto compounds of the formula IV

$$X-Z-NR^2-CHR^3-CO-(CHR^5)_n-CO-E \qquad IV$$

can be reduced to compounds of the formula I, for example with a complex metal hydride, such as NaBH$_4$, which does not simultaneously reduce the peptide carbonyl groups, in an inert solvent, such as methanol, at temperatures between about −10° and +30°. The compounds of the formula IV can be obtained, for example, by reaction of an amino acid of the formula X—Z—NR$^2$—CHR$^3$—COOH with carbonyldiimidazole to give the corresponding imidazolide and subsequent reaction with malonic acid derivatives of the formula HOOC—CH$_2$—CO—E or esters or salts thereof, followed by decarboxylation.

Compounds of the formula I can also be obtained by direct peptide synthesis from a carboxylic acid component and an amine component. Suitable carboxylic acid components are, for example, those of the part formula X—Z—OH, and suitable amine components are those of the part formula H—W—E. However, the peptide bond can also be linked within the group Z; a carboxylic acid of the formula X—Z$^1$—OH is thereby reacted with an amino peptide of the formula H—Z$^2$—W—E, Z$^1$+Z$^2$ being Z. The reaction is thereby advantageously carried out by customary methods of peptide synthesis, such as are described, for example, in Houben-Weyl, Loc. cit., Volume 15/II, pages 1 to 806 (1974).

The reaction is preferably carried out in the presence of a dehydrating agent, for example a carbodiimide, such as DCCI or dimethylaminopropylethyl-carbodiimide, or furthermore propanephosphonic acid anhydride (compare Angew. Chem. 92, 129 (1980)), diphenylphosphorylazide or 2-ethoxy-N-ethoxycarbonyl-1,2-dihydroquinoline, in an inert solvent, for example a halogenated hydrocarbon, such as methylene chloride, an ether, such as tetrahydrofuran or dioxane, an amide, such as DMF or dimethylacetamide, or a nitrile, such as acetonitrile, at temperatures between about $-10°$ and $40°$, preferably between $0°$ and $30°$.

Instead of II or III, it is also possible for suitable reactive derivatives of these substances to be employed in the reaction, for example those in which reactive groups are intermediately blocked by protective groups. The amino acid derivatives III can be used, for example, in the form of their activated esters, which are advantageously formed in situ, for example by addition of 1-hydroxybenzotriazole or N-hydroxysuccinimide.

The starting substances of the formulae II and III are known in most cases. Where they are not known, they can be prepared by known methods, for example by the abovementioned methods of peptide synthesis and of splitting off protective groups.

If desired, a functionally modified amino and/or hydroxyl group in a compound of the formula I can be liberated by solvolysis or hydrogenolysis by one of the methods described above.

Thus, in particular, a compound of the formula I wherein X is other than H can be converted into a compound of the formula I (X=H), advantageously by hydrogenolysis, if X=CBZ, and otherwise by selective solvolysis. If X is BOC, the BOC group can be split off, for example, with HCl in dioxane at room temperature.

It is furthermore possible to convert a radical E into another radical E by treatment with esterifying, solvolysing or amidating agents. Thus, an acid of the formula I (E=OH) can be esterified, for example with the aid of an alcohol of the formula A—OH or of a diazoalkane, for example diazomethane, or an ester of the formula I (E=OA) can be hydrolyzed to the corresponding acid of the formula I (E=OH), for example with sodium hydroxide in aqueous-dioxane solution at room temperature. It is furthermore possible, for example, for an ester of the formula I (E=OA) to be converted into the corresponding amide of the formula I (E=NH$_2$, NHA or NA$_2$) by treatment with ammonia or with an amine of the formula A—NH$_2$ or A$_2$NH.

A base of the formula I can be converted into the associated acid addition salt with an acid. Possible acids for this reaction are, in particular, acids which give physiologically acceptable salts. Thus, it is possible to use inorganic acids, for example sulfuric acid, nitric acid, hydrogen halide acid, such as hydrochloric acid or hydrobromic acid, phosphoric acids, such as orthophosphoric acid, or sulphamic acid, or furthermore organic acids, in particular aliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalene-mono- and -disulfonic acids and lauryl-sulfuric acid. Salts with physiologically unacceptable acids, for example picrates, can be used to isolate and/or purify the compounds of the formula I.

An acid of the formula I can be converted into one of its physiologically acceptable metal salts or ammonium salts by reaction with a base. Possible salts are, in particular, the sodium, potassium, magnesium, calcium and ammonium salts, and furthermore substituted ammonium salts, for example the dimethyl-, diethyl- or diisopropylammonium, monoethanol-, diethanol- and triethanolammonium, cyclohexylammonium, dicyclohexylammonium and dibenzylethylenediammonium salts, and furthermore, for example, salts with N-methyl-D-glucamine or with basic amino acids, such as arginine or lysine.

The new compounds of the formula I and their physiologically acceptable salts can be used for the preparation of pharmaceutical products by being brought into a suitable dosage form with at least one excipient or auxiliary and, if desired, together with one or more other active compound(s). The formulations thus obtained can be used as medicaments in human and veterinary medicine. Possible excipient substances are organic or inorganic substances which are suitable for enteral (for example oral or rectal) or parenteral administration or for administration in the form of an inhalation spray and which do not react with the new compounds, for example water, vegetable oils, benzyl alcohols, polyethylene glycols, glycerol triacetate and other fatty acid glycerides, gelatine, soya lecithin, carbohydrates such as lactose or starch, magnesium stearate, talc, cellulose. Particularly suitable for oral use are tablets, coated tablets, capsules, syrups, juices or drops; tablets and capsules with coatings resistant to gastric juice are of special interest. Suppositories are used for rectal administration and solutions, preferably oily or aqueous solutions, and furthermore suspensions, emulsions or implants are used for parenteral administration. Sprays which contain the active compound either dissolved or suspended in a propellant gas mixture (for example fluoro-chloro-hydrocarbons) can be used for administration as an inhalation spray. The active compound is advantageously thereby used in micronized form, it being possible for one or more additional physiologically acceptable solvents, for example ethanol, to be present. Inhalation solutions can be administered with the aid of customary inhalers. The new compounds can also be lyophilized and the resulting lyophilizates can be used, for example, for the preparation of injection products. The formulations mentioned can be sterilized and/or can contain auxiliaries, such as preservatives, stabilizers, wetting agents, emulsifiers, salts for influencing the osmotic pressure, buffer substances, dyestuffs and/or aroma substances. If desired, they can also contain one or more other active compounds, for example one or more vitamins.

The substances according to the invention are as a rule administered analogously to other known commercially available peptides, but in particular analogously to the compounds described in European Patent A-77,028, preferably in dosages between about 100 mg and 30 g, in particular between 500 mg and 5 g per dosage unit. The daily dosage is preferably between about 2 and 600 mg/kg of body weight. The specific dose for each particular patient depends, however, on the most diverse factors, for example on the activity of the specific compound employed, on the age, body weight, general state of health and sex, on the diet, on the time of administration and the administration route, and on the rate of excretion, the medicament combination and the severity of the particular disease to which the therapy applies. Parenteral administration is preferred.

Renin-associated hypertension and hyperaldosteronism are effectively treated by administration of from 10 to 300 mg/kg of body weight. For diagnostic purposes, the novel peptides may be administered in a single dose of from 0.1 to 10 mg/kg of body weight.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight; unless otherwise indicated.

All the temperatures above and below are given in °C. In the following examples, "customary working up" means: water is added, if necessary, the pH is adjusted to the stated value by addition of HCl or NaOH, the mixture is extracted with ether or methylene chloride, the organic phase is separated off, dried over sodium sulphate, filtered and evaporated and the residue is purified by chromatography on silica gel and/or crystallization.

EXAMPLE 1

A mixture of 1 g of 4S-[N-tert.-butoxycarbonyl-L-phenylalanyl-N(imi)-(2,4-dinitrophenyl)-L-histidyl]-3S-hydroxy-5-cyclohexylpentanoic acid ["BOC-Phe-(imi-DNP-His)-AHCP-OH"; obtainable by reaction of AHCP-OMe with BOC-(imi-DNP-His)-OH to give BOC-(imi-DNP-His)-AHCP-OMe, hydrolysis to give H-(imi-DNP-His)-AHCP-OMe, reaction with BOC-Phe-OH to give BOC-Phe-(imi-DNP-His)-AHCP-OMe and hydrolysis with NaOH in dioxane/water], 2 g of 2-mercaptoethanol, 25 ml of DMF and 25 ml of water is brought to pH 8 at 20°, while stirring, and is stirred at 20° for 2 hours. Customary working up (pH 3.5) gives 4S-(N-tert.-butoxycarbonyl-L-phenylalanyl-L-histidyl)-3S-hydroxy-5-cyclohexylpentanoic acid ("BOC-Phe-His-AHCP-OH"), m.p. 206° (decomposition).

The following compounds are obtained analogously from the corresponding imi-DNP-His derivatives:
acetyl-Phe-His-AHCP-OH
isobutyryl-Phe-His-AHCP-OH
isovaleryl-Phe-His-AHCP-OH
benzoyl-Phe-His-AHCP-OH
phenylacetyl-Phe-His-AHCP-OH
α-naphthylacetyl-Phe-His-AHCP-OH
3-phenylpropionyl-Phe-His-AHCP-OH
3-p-tolylpropionyl-Phe-His-AHCP-OH
3-o-methoxyphenylpropionyl-Phe-His-AHCP-OH
3-p-methoxyphenylpropionyl-Phe-His-AHCP-OH
3-p-fluorophenylpropionyl-Phe-His-AHCP-OH
3-p-chlorophenylpropionyl-Phe-His-AHCP-OH
3-p-bromophenylpropionyl-Phe-His-AHCP-OH
3-p-iodophenylpropionyl-Phe-His-AHCP-OH
3-m-trifluoromethylphenylpropionyl-Phe-His-AHCP-OH
cyclopropylcarbonyl-Phe-His-AHCP-OH
cyclopentylcarbonyl-Phe-His-AHCP-OH
cyclohexylcarbonyl-Phe-His-AHCP-OH
3-cyclohexylpropionyl-Phe-His-AHCP-OH
6-cycloheptylhexanoyl-Phe-His-AHCP-OH
POA-Phe-His-AHCP-OH
CBZ-Ada-His-AHCP-OH
CBZ-Cal-His-AHCP-OH
CBZ-αNal-His-AHCP-OH
CBZ-βNal-His-AHCP-OH
CBZ-Phe-His-AHCP-OH
CBZ-Trp-His-AHCP-OH
CBZ-Tyr-His-AHCP-OH
2-benzyl-3-phenylpropionyl-Phe-His-AHCP-OH
4-phenylbutyryl-Phe-His-AHCP-OH
2-benzyl-4-phenylbutyryl-Phe-His-AHCP-OH
2-(2-phenylethyl)-4-phenylbutyryl-Phe-His-AHCP-OH
2-(2-naphthylmethyl)-4-phenylbutyryl-Phe-His-AHCP-OH

EXAMPLE 2

1 g of BOC-Phe-(imi-BOM-His)-AHCP-OH [m.p. 198°; obtainable by reaction of AHCP-OMe with BOC-(imi-BOM-His)-OH to give BOC-(imi-BOM-His)-AHCP-OMe (m.p. 116°), hydrolysis to give H-(imi-BOM-His)-AHCP-OMe (hydrochloride, m.p. 123°), reaction with BOC-Phe-OH to give BOc-Phe-(imi-BOM-His)-AHCP-OMe (m.p. 74°) and hydrolysis with NaOH in aqueous dioxane] is dissolved in 10 ml of methanol and hydrogenated on 0.5 g of 5% Pd-C at 20° under 1 bar, the mixture is filtered and the filtrate is evaporated to give BOC-Phe-His-AHCP-OH, m.p. 206° (decomposition).

The same substance can also be obtained from the same starting substance by treatment with ammonium formate/10% Pd-C in methanol at 20°.

The following compounds are obtained analogously from the corresponding imi-BOM derivatives:
BOC-His-AHCP-OH
BOC-Phe-His-AHCP-OMe
BOC-Phe-His-AHCP-OEt
BOC-Phe-His-AHCP-NH$_2$, m.p. 198° (decomposition)
BOC-Phe-His-AHCP-NHCH$_3$
BOC-Phe-His-AHCP-N(CH$_3$)$_2$, m.p. 189° (decomposition)
BOC-Abu-His-AHCP-OH
BOC-Ada-His-AHCP-OH
BOC-Ala-His-AHCP-OH
BOC-Arg-His-AHCP-OH
BOC-Asn-His-AHCP-OH
BOC-Bia-His-AHCP-OH
BOC-Cal-His-AHCP-OH, m.p. 152°–154°
BOC-Dab-His-AHCP-OH
BOC-Gln-His-AHCP-OH
BOC-Gly-His-AHCP-OH
BOC-His-His-AHCP-OH
BOC-N(im)-methyl-His-His-AHCP-OH
BOC-Ile-His-AHCP-OH
BOC-Leu-His-AHCP-OH
BOC-tert.-Leu-His-AHCP-OH
BOC-Lys-His-AHCP-OH
BOC-Met-His-AHCP-OH
BOC-αNal-His-AHCP-OH, m.p. 163°–165°
BOC-βNal-His-AHCP-OH, m.p. 187°
  [from BOC-β-Nal-(imi-BOM-His)-AHCP-OMe (m.p. 92°–94°) via BOC-β-Nal-(imi-BOM-His)-AHCP-OH (m.p. 174°–176°)]
BOC-Nbg-His-AHCP-OH
BOC-Nle-His-AHCP-OH
BOC-Orn-His-AHCP-OH
BOC-Phe-His-AHCP-OH
BOC-Pro-His-AHCP-OH BOC-Ser-His-AHCP-OH
BOC-Thr-His-AHCP-OH
BOC-Tic-His-AHCP-OH
BOC-Trp-His-AHCP-OH
BOC-Tyr-His-AHCP-OH
BOC-Val-His-AHCP-OH
(2-benzyl-4-phenylbutyryl-His)-AHCP-OH, m.p. 191°
 [decomposition; obtainable from H-(imi-BOM-His)-AHCP-OMe via (2-benzyl-4-phenylbutyryl-imi-BOM-His)-AHCP-OMe (m.p. 125°–128°) and (2-benzyl-4-phenylbutyryl-imi-BOM-His)-AHCP-OH (m.p. 184°)]
[2-(2-phenylethyl)-4-phenylbutyryl-His]-AHCP-OH
(2-benzyl-3-phenylpropionyl-His)-AHCP-OH  [2-(2-naphthylmethyl)-4-phenylbutyryl-His]-AHCP-OH
(2-benzyl-4-phenylbutyryl-His)-AHCP-N(CH$_3$)$_2$, m.p. 73°–75°
POA-His-AHCP-OH
BOC-Phe-His-AHCP-OH
BOC-Phe-His-AHCH-OMe
BOC-Phe-His-AHCH-OEt
BOC-Phe-His-AHCH-NH$_2$
BOC-Phe-His-AHCH-NHCH$_3$
BOC-Phe-His-AHCH-N(CH$_3$)$_2$
N-ethylcarbamoyl-Phe-His-AHCP-NHCH$_2$CH$_2$CH(CH$_3$)$_2$
N-isopropylcarbamoyl-Phe-His-AHCP-NHCH$_2$CH$_2$CH(CH$_3$)$_2$
N-isopropylcarbamoyl-Phe-His-AHCP-NHCH$_2$CH(CH$_3$)C$_2$H$_5$
N-isopropylcarbamoyl-Phe-His-AHCP-N(CH$_3$)$_2$
N-isopropylcarbamoyl-Phe-His-AHCP-OH
morpholinocarbonyl-Phe-His-AHCP-OH, m.p. 150° (decomposition)
morpholinocarbonyl-Phe-His-AHCP-NHCH$_2$CH$_2$CH(CH$_3$)$_2$
morpholinocarbonyl-Phe-His-AHCP-NHCH$_2$CH(CH$_3$)C$_2$H$_5$, m.p. 110°–112°.

EXAMPLE 3

1.01 g of N-methylmorpholine are added to a solution of 2.66 of AHCP methyl ester hydrochloride in 50 ml of methylene chloride. 3.78 g of BOC-Phe-NLe-OH, 1.35 g of HOBt and a solution of 2.06 g of DCCI in 50 ml of methylene chloride are added, the mixture is stirred at 4° for 14 hours, the dicyclohexylurea which has precipitated is filtered off, the filtrate is evaporated and the residue is worked up in the customary manner (pH 8). BOC-Phe-Nle-AHCP-OMe, m.p. 179°, is obtained.

The following compounds are obtained analogously with the corresponding BOC-peptides:
BOC-Phe-Abu-AHCP-OMe
BOC-Phe-Ada-AHCP-OMe
BOC-Phe-Ala-AHCP-OMe
BOC-Phe-Arg-AHCP-OMe
BOC-Phe-Asn-AHCP-OMe
BOC-Phe-Bia-AHCP-OMe, m.p. 95°–98°
BOC-Phe-Cal-AHCP-OMe
BOC-Phe-Dab-AHCP-OMe
BOC-Phe-Gln-AHCP-OMe
BOC-Phe-Gly-AHCP-OMe, m.p. 73°–76°
BOC-Phe-His-AHCP-OMe
BOC-Phe-N(im)-methyl-His-AHCP-OMe
BOC-Phe-Ile-AHCP-OMe
BOC-Phe-Leu-AHCP-OMe
BOC-Phe-tert.-Leu-AHCP-OMe
BOC-Phe-Lys-AHCP-OMe
BOC-Phe-Met-AHCP-OMe
BOC-Phe-Nal-AHCP-OMe
BOC-Phe-Nal-AHCP-OMe
BOC-Phe-Nbg-AHCP-OMe
BOC-Phe-Orn-AHCP-OMe
BOC-Phe-AHCP-OMe
BOC-Phe-Pro-AHCP-OMe
BOC-Phe-Ser-AHCP-OMe
BOC-Phe-Thr-AHCP-OMe
BOC-Phe-Tic-AHCP-OMe
BOC-Phe-Trp-AHCP-OMe
BOC-Phe-Tyr-AHCP-OMe
BOC-Phe-Val-AHCP-OMe
BOC-Abu-His-AHCP-OMe
BOC-Ada-His-AHCP-OMe
BOC-Ala-His-AHCP-OMe
BOC-Arg-His-AHCP-OMe
BOC-Asn-His-AHCP-OMe
BOC-Bia-His-AHCP-OMe
BOC-Cal-His-AHCP-OMe
BOC-Dab-His-AHCP-OMe
BOC-Gln-His-AHCP-OMe
BOC-Gly-His-AHCP-OMe
BOC-His-His-AHCP-OMe
BOC-N(im)-methyl-His-His-AHCP-OMe
BOC-Ile-His-AHCP-OMe
BOC-Leu-His-AHCP-OMe
BOC-tert.Leu-His-AHCP-OMe
BOC-Lys-His-AHCP-OMe
BOC-Met-His-AHCP-OMe
BOC-αNal-His-AHCP-OMe
BOC-βNal-His-AHCP-OMe
BOC-Nbg-His-AHCP-OMe
BOC-Nle-His-AHCP-OMe
BOC-Orn-His-AHCP-OMe
BOC-Phe-His-AHCP-OMe
BOC-Pro-His-AHCP-OMe
BOC-Ser-His-AHCP-OMe
BOC-Thr-His-AHCP-OMe
BOC-Tic-His-AHCP-OMe
BOC-Trp-His-AHCP-OMe
BOC-Tyr-His-AHCP-OMe
BOC-Val-His-AHCP-OMe
BOC-Phe-Gly-AHCP-NH-CH$_2$CH(CH$_3$)$_2$, m.p. 84°–86°
BOC-Phe-Gly-AHCP-NH-CH$_2$CH$_2$CH(CH$_3$)$_2$, m.p. 87°–89°
BOC-Phe-Gly-AHCP-NH-CH$_2$CH(CH$_3$)C$_2$H$_5$
morpholinocarbonyl-Phe-Gly-AHCP-OH, m.p. 88°–90°
morpholinocarbonyl-Phe-Gly-AHCP-NH-CH$_2$CH(CH$_3$)$_2$
morpholinocarbonyl-Phe-Gly-AHCP-NH-CH$_2$CH$_2$CH(CH$_3$)$_2$
morpholinocarbonyl-Phe-Gly-AHCP-NH-CH$_2$CH(CH$_3$)C$_2$H$_5$, m.p. 116°–118°.

Example 4

BOC-Phe-Nle-AHCP-NH$_2$ is obtained analogously to Example 3 from BOC-Phe-OH and H-Nle-AHCP-NH$_2$ hydrochloride/N-methylmorpholine/HOBt/DCCI.

BOC-Phe-Nle-AHCP-OMe, m.p. 179°, is obtained analogously with H-Nle-AHCP-OMe (which can be prepared from BOC-Nle-AHCP-OMe, Rf 0.9 on silica gel, CH$_2$Cl$_2$/CH$_3$OH 9:1).

Example 5

BOC-Phe-Met-AHCP-N(CH₃)₂ is obtained analogously to Example 3 from BOC-Phe-Met-AHCP-OH and dimethylamine hydrochloride/N-methylmorpholine/HOBt/DCCI.

Example 6

A solution of 1 g of BOC-Phe-His-AHCP-OH in 20 ml of 4N HCl in dioxane is stirred at 20° for 30 minutes and then evaporated. Customary working up gives H-Phe-His-AHCP-OH.

The following compounds are obtained analogously by splitting the corresponding BOC derivatives:
H-Phe-His-AHCP-OMe
H-Phe-His-AHCP-OEt
H-Phe-His-AHCP-NH₂
H-Phe-His-AHCP-NHCH₃
H-Phe-His-AHCP-N(CH₃)₂
H-Abu-His-AHCP-OH
H-Ada-His-AHCP-OH
H-Ala-His-AHCP-OH
H-Arg-His-AHCP-OH
H-Asn-His-AHCP-OH
H-Bia-His-AHCP-OH
H-Cal-His-AHCP-OH
H-Dab-His-AHCP-OH
H-Gln-His-AHCP-OH
H-Gly-His-AHCP-OH
H-His-His-AHCP-OH
H-N(im)-methyl-His-His-AHCP-OH
H-Ile-His-AHCP-OH
H-Leu-His-AHCP-OH
H-tert.-Leu-His-AHCP-OH
H-Lys-His-AHCP-OH
H-Met-His-AHCP-OH
H-αNal-His-AHCP-OH
H-βNal-His-AHCP-OH
H-Nbg-His-AHCP-OH
H-Nle-His-AHCP-OH
H-Orn-His-AHCP-OH
H-Phe-His-AHCP-OH
H-Pro-His-AHCP-OH
H-Ser-His-AHCP-OH
H-Thr-His-AHCP-OH
H-Tic-His-AHCP-OH
H-Trp-His-AHCP-OH
H-Tyr-His-AHCP-OH
H-Val-His-AHCP-OH
H-Phe-Ada-AHCP-OH
H-Phe-Asn-AHCP-OH
H-Phe-Bia-AHCP-OH
H-Phe-Cal-AHCP-OH
H-Phe-Dab-AHCP-OH
H-Phe-Gln-AHCP-OH
H-Phe-Gly-AHCP-OH
H-Phe-N(im)-methyl-His-AHCP-OH
H-Phe-Ile-AHCP-OH
H-Phe-Leu-AHCP-OH
H-Phe-tert.-Leu-AHCP-OH
H-Phe-Lys-AHCP-OH
H-Phe-Met-AHCP-OH
H-Phe-αNal-AHCP-OH
H-Phe-βNal-AHCP-OH
H-Phe-Nbg-AHCP-OH
H-Phe-Nle-AHCP-OH
H-Phe-Orn-AHCP-OH
H-Phe-Phe-AHCP-OH
H-Phe-Pro-AHCP-OH
H-Phe-Ser-AHCP-OH
H-Phe-Thr-AHCP-OH
H-Phe-Tic-AHCP-OH
H-Phe-Trp-AHCP-OH
H-Phe-Tyr-AHCP-OH
H-Phe-Val-AHCP-OH.

Example 7

20 ml of 2N sodium hydroxide solution are added to a solution of 1 g of BOC-Phe-His-AHCP-OMe [obtainable by hydrogenolysis of BOC-Phe-(imi-BOM-His)-AHCP-OMe] in 20 ml of dioxane. The mixture is stirred at 20° C. for 2 hours and brought to pH 3.5 and the resulting BOC-Phe-His-AHCP-OH is filtered off; m.p. 206° (decomposition).

The free carboxylic acids listed in Example 2 and the following compounds are obtained analogously by hydrolysis of the corresponding methyl esters:
BOC-Phe-Abu-AHCP-OH
BOC-Phe-Ada-AHCP-OH
BOC-Phe-Ala-AHCP-OH
BOC-Phe-Arg-AHCP-OH
BOC-Phe-Asn-AHCP-OH
BOC-Phe-Bia-AHCP-OH
BOC-Phe-Cal-AHCP-OH
BOC-Phe-Dab-AHCP-OH
BOC-Phe-Gln-AHCP-OH, decomposition at 104°-106°
BOC-Phe-Gly-AHCP-OH
BOC-Phe-N(im)-methyl-His-AHCP-OH
BOC-Phe-Ile-AHCP-OH
BOC-Phe-Leu-AHCP-OH
BOC-Phe-tert.-Leu-AHCP-OH
BOC-Phe-Lys-AHCP-OH
BOC-Phe-Met-AHCP-OH
BOC-Phe-αNal-AHCP-OH
BOC-Phe-βNal-AHCP-OH
BOC-Phe-Nbg-AHCP-OH
BOC-Phe-Nle-AHCP-OH, m.p. 196°
BOC-Phe-Orn-AHCP-OH
BOC-Phe-Phe-AHCP-OH
BOC-Phe-Pro-AHCP-OH
BOC-Phe-Ser-AHCP-OH
BOC-Phe-Thr-AHCP-OH
BOC-Phe-Tic-AHCP-OH
BOC-Phe-Trp-AHCP-OH
BOC-Phe-Tyr-AHCP-OH
BOC-Phe-Val-AHCP-OH.

Example 8

A mixture of 1 g of BOC-Phe-His-AHCP-OMe, 3 g of NH₄Cl and 100 ml of saturated methanolic NH₃ solution is left to stand at 20° for 4 days. It is evaporated and the residue is worked up in the customary manner (pH 7) to give BOC-Phe-His-AHCP-NH₂, m.p. 198° (decomposition).

Reaction of the corresponding esters with NH₃ or the corresponding alkyl- or dialkylamines gives, analogously, the corresponding amides, for example
BOC-Phe-His-AHCP-NHCH₃
BOC-Phe-His-AHCP-NHC₂H₅
BOC-Phe-His-AHCP-NHC₄H₉
BOC-Phe-His-AHCP-NH-CH₂-CH₂CH(CH₃)₂, m.p. 171°-173°
BOC-Phe-His-AHCP-N(CH₃)₂
BOC-Phe-His-AHCP-N(C₂H₅)₂

BOC-Phe-His-AHCP-N(C$_4$H$_9$)$_2$
BOC-Phe-Abu-AHCP-NH$_2$
BOC-Phe-Dab-AHCP-NH$_2$
BOC-Phe-Lys-AHCP-NH$_2$
BOC-Phe-Met-AHCP-NH$_2$
BOC-Phe-N(im)-methyl-His-AHCP-NH$_2$
BOC-Phe-Nle-AHCP-NH$_2$
BOC-Phe-Orn-AHCP-NH$_2$
BOC-Ada-His-AHCP-NH$_2$
BOC-Cal-His-AHCP-NH$_2$
BOC-Nal-His-AHCP-NH$_2$
BOC-Nal-His-AHCP-NH$_2$
BOC-Trp-His-AHCP-NH$_2$
BOC-Tyr-His-AHCP-NH$_2$
BOC-Phe-Abu-AHCP-N(CH$_3$)$_2$
BOC-Phe-Dab-AHCP-N(CH$_3$)$_2$
BOC-Phe-Lys-AHCP-N(CH$_3$)$_2$
BOC-Phe-Met-AHCP-N(CH$_3$)$_2$
BOC-Phe-N(im)-methyl-His-AHCP-N(CH$_3$)$_2$
BOC-Phe-Nle-AHCP-N(CH$_3$)$_2$
BOC-Phe-Orn-AHCP-N(CH$_3$)$_2$
BOC-Ada-His-AHCP-N(CH$_3$)$_2$
BOC-Cal-His-AHCP-N(CH$_3$)$_2$
BOC-αNal-His-AHCP-N(CH$_3$)$_2$
BOC-βNal-His-AHCP-N(CH$_3$)$_2$
BOC-Trp-His-AHCP-N(CH$_3$)$_2$
BOC-Tyr-His-AHCP-N(CH$_3$)$_2$.

Example 9

1 g of CBZ-Phe-His-AHCP-OH is dissolved in 10 ml of methanol and hyrogenated on 0.5 g of 10% Pd-C at 20° under 1 bar for 3 hours, the mixture is filtered and the filtrate is evaporated to give H-Phe-His-AHCP-OH.

The compounds listed in Example 6 can be obtained analogously from the corresponding CBZ derivatives.

The following examples relate to pharmaceutical formulations.

Example A: Injection glasses

A solution of 100 g of BOC-Phe-His-AHCP-OH and 5 g of disodium hydrogen phosphate in 3 ml of doubly-distilled water is brought to pH 6.5 with 2N hydrochloric acid, filtered sterile, bottled in injection glasses, lyophilized under sterile conditions and sealed sterile. Each injection glass contains 500 mg of active compound.

Example B: Suppositories

A mixture of 500 g of BOC-Phe-His-AHCP-OH with 100 g of soya lecithin and 1,400 g of cocoa butter is melted, poured into molds and allowed to cool. Each suppository contains 500 mg of active compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A peptide compound of the formula I $$X-Z-NR^2-CHR^3-CHOH-(CHR^4)_n-CO-E \quad I$$

wherein

X is H, $R^1-O-C_mH_{2m}-CO-$, $R^1-C_mH_{2m}-O-CO-$, $R^1-C_mH_{2m}-CO-$, $R^1-SO_2-$, $(R^1-C_mH_{2m})-L(R^1-C_pH_{2p})-C_rH_{2r}-CO-$, $H-(NHCH_2CH_2)_m-$ $NH-CH_2CO-$ or 9-fluorenyl-$C_mH_{2m}-O-CO-$, Z is 1 to 4 amino acid radicals which are bonded to one another in peptide form and chosen independently from Abu, Ada, Ala, Arg, Asn, Bia, Cal, Dab, Gln, Gly, His, N(im)-alkyl-His, Ile, Leu, tert.-Leu, Lys, Met, α-Nal, βNal, Nbg, Nle, Orn, Phe, Pro, Ser, Thr, Tic, Trp, Tyr, and Val, is OH, OA, NH$_2$, NHA or NA$_2$, R$^1$ is H, A, Ar, Ar-alkyl, cycloalkyl which has 3 to 7 C atoms and is unsubstituted or mono- or polysubstituted by alkyl, alkoxy and/or Hal, cycloalkylalkyl with 4–11 C atoms, bicycloalkyl or tricycloalkyl with in each case 7–14 C atoms or bicycloalkylalkyl or tricycloalkylalkyl with in each case 8–18 C atoms, wherein the group $(R^1-C_mH_{2m})-L(R^1-C_pH_{2p})$ also can be pyrrolidino, piperidino, morpholino or thiomorpholino, R$^2$ and R$^4$ are each independently H or A, R$^3$ is cycloalkylalkyl, bicycloalkylalkyl or tricycloalkylalkyl with in each case up to 18 C atoms, L is CH or N, m, p and r are each independently, 0, 1, 2, 3, 4 or 5, n is 1 or 2, Ar is phenyl, naphthyl or phenyl substituted by A, AO, Hal, CF$_3$, OH or NH$_2$, Hal is F, Cl, Br or I and A is alkyl of 1–8 C atoms, wherein one or more —NH—CO— groups can be replaced by —N(alkyl)—CO— groups, and wherein A and Hal groups can be the same or different, or a pharmaceutically acceptable salt thereof with the proviso that E is OH, Oalkyl of 5–8 C atoms, NHA or NA$_2$ when at the same time Z is (Pro)$_x$-Y, x is 0 or 1, Y is Phe-Phe, Phe-His, Phe-Leu, Phe-Tyr, Phe-Nle, His-Phe, His-His, His-Leu, His-Tyr, His-Nle, Leu-Phe, Leu-His, Leu-Leu, Leu-Tyr, Leu-Nle, Tyr-Phe, Tyr-His, Tyr-Leu, Tyr-Tyr, Tyr-Nle, αNal-Phe, αNal-His, αNal-Leu, αNal-Tyr or αNal-Nle, R$^2$ and R$^4$ are each H, R$^3$ is cycloalkylalkyl with 5–10 C atoms, and n is 1.

2. A compound of claim 1, wherein A is an alkyl of 1–4 C atoms.

3. A compound of claim 1, wherein Ar is phenyl.

4. A compound of claim 1, wherein R$^1$ is A.

5. A compound of claim 1, wherein R$^2$ and R$^4$ are each independently H or methyl.

6. A compound of claim 1, wherein R$^3$ is cyclohexylmethyl.

7. A compound of claim 1, wherein m, p and r are independently 0, 1 or 2 and n is 1.

8. A compound of claim 1, wherein X is H, POA, BOC, CBZ, acetyl, propionyl, butyryl, isobutyryl, cyclopentylcarbonyl, cyclohexylcarbonyl, benzoyl, phenylacetyl, 2- or 3-phenylpropionyl, 4-phenylbutyryl, 2-benzyl-3-phenylpropionyl, 2-benzyl-4-phenylbutyryl, 2-(2-phenylethyl)-4-phenylbutyryl, 2-(2-naphthylmethyl)-4-phenylbutyryl, 2 or 3-o-, -m- or -p-fluorophenylpropionyl, 2- or 3-o-, -m- or -p-chlorophenylpropionyl, cyclohexylacetyl or 2- or 3-cyclohexylpropionyl, wherein POA is phenoxyacetyl, BOC is tert.-butoxycarbonyl and CBZ is benzyloxycarbonyl.

9. A compound of claim 1, wherein Z is His, Phe-His, Pro-Phe-His or His-Pro-Phe-His.

10. A compound of claim 1, wherein Z is Abu, Ada, Asn, Bia, Cal, Gln, N-(im)-alkyl-His, Leu, αNal, βNal, Nle, Phe, Trp, Tyr, Abu-His, Ada-His, Ala-His, Ala-Phe, Arg-His, Asn-His, Bia-His, Cal-His, Dab-His, Gly-His, His-His, Ile-His, Leu-His, tert.-Leu-His, Lys-His, Met-His, αNal-His, βNal-His, Nbg-His, Nle-His, (N-Me-His)-His, (N-Me-Phe)-His, Orn-His, Phe-Abu, Phe-Ada, Phe-Ala, Phe-Arg, Phe-Asn, Phe-Bia, Phe-Cal, Phe-Dab, Phe-Gln, Phe-Gly, Phe-(N-im-alkyl-His), Phe-Ile, Phe-Leu, Phe-tert.-Leu, Phe-Lys, Phe-Met, Phe-α-Nal, Phe-βNal, Phe-Nbg, Phe-Nle, Phe-(N-Me-His), Phe-(N-Me-Phe), Phe-Orn, Phe-Phe, Phe-Pro, Phe-Ser, Phe-Thr, Phe-Tic, Phe-Trp, Phe-Tyr, Phe-Val, Pro-His, Ser-His, Thr-His, Tic-His, Trp-His, Tyr-His, Val-His, Ada-Phe-His, Pro-Ala-His, Pro-Ala-Phe, Pro-Phe-Ala, Pro-Phe-Phe, His-Pro-Ala-His, His-Pro-Ala-Phe, His-Pro-Phe-Ala, His-Pro-Phe-Phe, Pro-Abu-His, Pro-Ada-His, Pro-Arg-His, Pro-Asn-His, Pro-Bia-His, Pro-Dab-His, Pro-Gly-His, Pro-His-His, Pro-Ile-His, Pro-Leu-His, Pro-tert.-Leu-His, Pro-Lys-His, Pro-Met-His, Pro-Nbg-His, Pro-Nle-His, Pro-(N-Me-His)-His, Pro-(N-Me-Phe)-His, Pro-Orn-His, Pro-Phe-Abu, Pro-Phe-Ada, Pro-Phe-Arg, Pro-Phe-Asn, Pro-Phe-Bia, Pro-Phe-Dab, Pro-Phe-Gln, Pro-Phe-Gly, Pro-Phe-(N-im-alkyl-His), Pro-Phe-Ile, Pro-Phe-Leu, Pro-Phe-tert.-Leu, Pro-Phe-Lys, Pro-Phe-Met, Pro-Phe-Nbg, Pro-Phe-Nle, Pro-Phe-(N-Me-His), Pro-Phe-(N-Me-Phe), Pro-Phe-Orn, Pro-Phe-Pro, Pro-Phe-Ser, Pro-Phe-Thr, Pro-Phe-Tic, Pro-Phe-Trp, Pro-Phe-Tyr, Pro-Phe-Val, Pro-Pro-His, Pro-Ser-His, Pro-Thr-His, Pro-Tic-His, Pro-Trp-His, Pro-Tyr-His, Pro-Val-His, His-Pro-Abu-His, His-Pro-Ada-His, His-Pro-Arg-His, His-Pro-Asn-His, His-Pro-Bia-His, His-Pro-Dab-His, His-Pro-Gly-His, His-Pro-His-His, His-Pro-Ile-His, His-pro-Leu-His, His-Pro-tert.-Leu-His, His-Pro-Lys-His, His-Pro-Met-His, His-Pro-Nbg-His, His-Pro-Nle-His, HiS-Pro-(N-Me-His)-His, His-Pro-(N-Me-Phe)-His, His-Pro-Orn-His, His-Pro-Phe-Abu, His-Pro-Phe-Ada, His-Pro-Phe-Arg, His-Pro-Phe-Asn, His-Pro-Phe-Bia, His-Pro-Phe-Dab, His-Pro-Phe-Gln, His-Pro-Phe-Gly, His-Pro-Phe(N-im-alkyl-His), His-Pro-Phe-Ile, His-Pro-Phe-Leu, His-Pro-Phe-tert.-Leu, His-Pro-Phe-Lys, His-Pro-Phe-Met, His-Pro-Phe-Nbg, His-Pro-Phe-Nle, His-Pro-Phe-(N-Me-His), His-Pro-Phe-(N-Me-Phe), His-Pro-Phe-Orn, His-Pro-Phe-Pro, His-Pro-Phe-Ser, His-Pro-Phe-Thr, His-Pro-Phe-Tic, His-Pro-Phe-Trp, His-Pro-Phe-Tyr, His-Pro-Phe-Val, His-Pro-Pro-His, His-Pro-Ser-His, His-Pro-Thr-His, His-Pro-Tic-His, His-Pro-Trp-His, His-Pro-Tyr-His or His-Pro-Val-His.

11. A compound of claim 1, wherein E is OH, $OCH_3$, $OC_2H_5$, $NH_2$, $NHCH_3$ or $N(CH_3)_2$.

12. A compound of claim 1, wherein —$NR^3$—$CHR^3$—$CHOH$—$(CHR^4)_n$—$CO$— is —$NH$—$CHR^3$—$CHOH$— $CH_2$—$CO$—, —$NH$—$CH$(cyclohexylmethyl)—$CHOH$—$CH_2$—$CO$— or —$NH$—$CH$—$(CH_2CH_2$-cyclohexyl)—cyclohexyl)—$CHOH$—$CH_2$—$CO$—.

13. A compound of claim 1, wherein
X is H, phenoxyacetyl, tert.-butoxycarbonyl, 4-phenylbutyryl, 2-benzyl-3-phenylpropionyl, 2-benzyl-4-phenylbutyryl, 2-(2-phenylethyl)-4-phenylbutyryl, 2-(2-naphthylmethyl)-4-phenylbutyryl or benzyloxycarbonyl, Z is His, Ada-His, Cal-His, Nle-His, Phe-Abu, Phe-Dab, Phe-His, Phe-Lys, Phe-Met, Phe-(N-immethyl)-His, Phe-Nle, Phe-Orn, Pro-Phe-His or His-Pro-Phe-His, $R^2$ and $R^4$ are each H, $R^3$ is cyclohexylmethyl or 2-cyclohexylethyl, E is OH, $OCH_3$, $OC_2H_5$, $NH_2$, $NH(CH_3)$ or $N(CH_3)_2$ and n is 1.

14. A compound of claim 1, wherein
X is H, tert.-butoxycarbonyl, 2-benzyl-3-phenylpropionyl, 2-benzyl-4-phenylbutyryl, 2-(2-phenylethyl)-4-phenylbutyryl, or 2-(2-naphthylmethyl)-4-phenylbutyryl, Z is His, Ada-His, Cal-His, Nle-His, Phe-Abu, Phe-Dab, Phe-His, Phe-Lys, Phe-Met, Phe-(N-immethyl)-His, Phe-Nle, Phe-Orn, $R^2$ and $R^4$ are each H, $R^3$ is cyclohexylmethyl, E is OH, $OCH_3$, $OC_2H_5$, $NH_2$, $NH(CH_3)$ or $N(CH_3)_2$ and n is 1.

15. A compound of claim 1, wherein
X is H, tert.-butoxycarbonyl or 2-benzyl-4-phenylbutyryl, Z is His, Phe-Nle or Phe-His, $R^2$ and $R^4$ are each H, $R^3$ is cyclohexylmethyl, E is OH, $OCH_3$, $OCH_5$, $NH_2$, $NH(CH_3)$ or $N(CH_3)_2$ and n is 1.

16. A compound of claim 1, wherein
X is tert.-butoxycarbonyl or 2-benzyl-4-phenylbutyryl, Z is His, Phe-Nle or Phe-His, $R^2$ and $R^4$ are each H, $R^3$ is cyclohexylmethyl, E is OH, $OCH_3$, $NH_2$ or $N(CH_3)_2$ and n is 1.

17. A compound of claim 1, wherein
X is tert.-butoxycarbonyl or 2-benzyl-4-phenylbutyryl, Z is Phe-Nle or Phe-His, $R^2$ and $R^4$ are each H, $R^3$ is cyclohexylmethyl, E is OH or $OCH_3$ and n is 1.

18. A compound of claim 1, wherein
X is pyrrolidinocarbonyl, piperidinocarbonyl, morpholinocarbonyl or thiomopholinocarbonyl.

19. (a) 4-(BOC-Phe-His-amino)-5-cyclohexyl-3-hydroxypentanoic acid;

(b) 4-(BOC-Phe-Nle-amino)-5-cyclohexyl-3-hydroxypentanoic acid; or (c) 5-Cyclohexyl-3-hydroxy-4-(2-benzyl-4-phenylbutyryl-His-amino)-pentanoic acid, wherein BOC is tert.-butoxycarbonyl, and each is a compound of claim 1.

20. A pharmaceutical composition comprising a compound of claim 1, and a compatible carrier.

21. A composition of claim 20, wherein the amount of said compound is about 500 mg to 5 g.

22. A method of treating or preventing hypertension comprising administering a compound of claim 1.

23. A method of treating or preventing hyperaldosteronism comprising administering a compound of claim 1.

24. A method of treating or preventing a disease contributed to by renin, comprising administering a compound of claim 1.

* * * * *

UNITED STATES PATENT AND TRADEMARK OFFICE
CERTIFICATE OF CORRECTION

PATENT NO. : 4,812,555

DATED : March 14, 1989

INVENTOR(S) : RADDATZ ET AL

It is certified that error appears in the above-identified patent and that said Letters Patent is hereby corrected as shown below:

Column 18, claim 1, line 15:

reads "Pro, Ser, Thr, Tic, Trp, Tyr, and Val, is OH, OA,"

should read -- Pro, Ser, Thr, Tic, Trp, Tyr, and Val, --

Column 18, claim 1, line 16:

reads "$NH_2$, NHA or $NA_2$,"

should read -- E is OH, OA, $NH_2$, NHA or $NA_2$, --

Signed and Sealed this

Twenty-fourth Day of July, 1990

Attest:

HARRY F. MANBECK, JR.

*Attesting Officer*  *Commissioner of Patents and Trademarks*